United States Patent [19]

Ito

[11] 4,302,602

[45] Nov. 24, 1981

[54] 2-(N,N-DIMETHYLAMINO) INDAN-1,3-DIONE AND METHOD FOR MANUFACTURE THEREOF

[75] Inventor: Masaaki Ito, Hokkaido, Japan

[73] Assignee: Hokkaido Sugar Co., Ltd., Tokyo, Japan

[21] Appl. No.: 166,788

[22] Filed: Jul. 8, 1980

[30] Foreign Application Priority Data

Jul. 17, 1979 [JP] Japan .................................. 54-89885

[51] Int. Cl.$^3$ ............................................. C07C 87/28
[52] U.S. Cl. .................................................. 564/428
[58] Field of Search ......................... 260/577; 564/428

[56] References Cited

U.S. PATENT DOCUMENTS 3,980,707 9/1976 Vanags et al. ...................... 260/577
4,207,335 6/1980 Buckle et al. ....................... 564/428

OTHER PUBLICATIONS

"Chemical Abstracts", 90, 214,745d, 1979.

Primary Examiner—Paul F. Shaver
Attorney, Agent, or Firm—Oblon, Fisher, Spivak, McClelland & Maier

[57] ABSTRACT

A novel compound, 2-(N,N-dimethyamino) indan-1,3-dione, is useful as an ultraviolet absorbent and is produced from salicylaldehyde, betaine and acetic anhydride.

3 Claims, 5 Drawing Figures

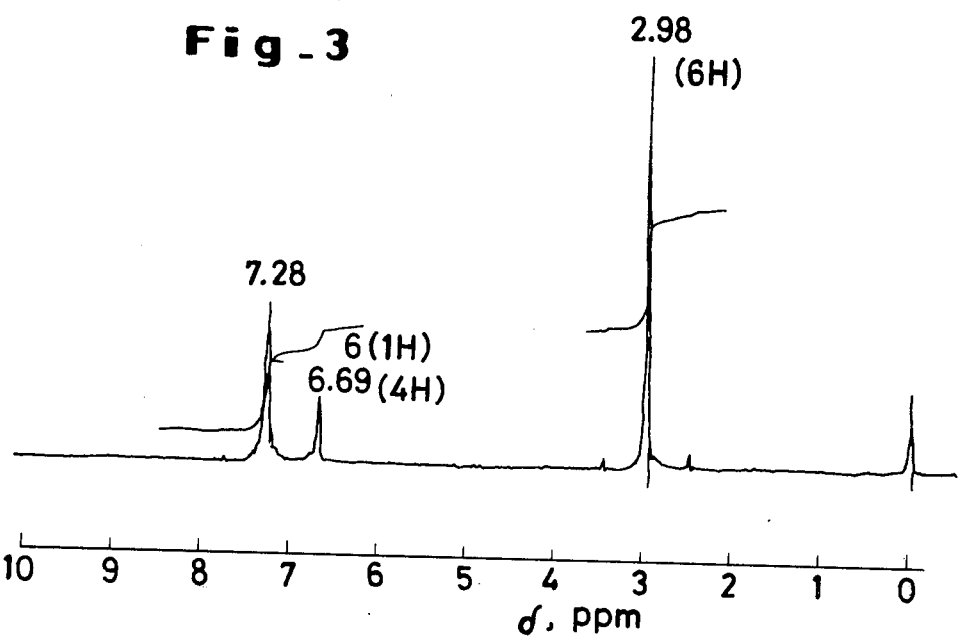
Fig_3
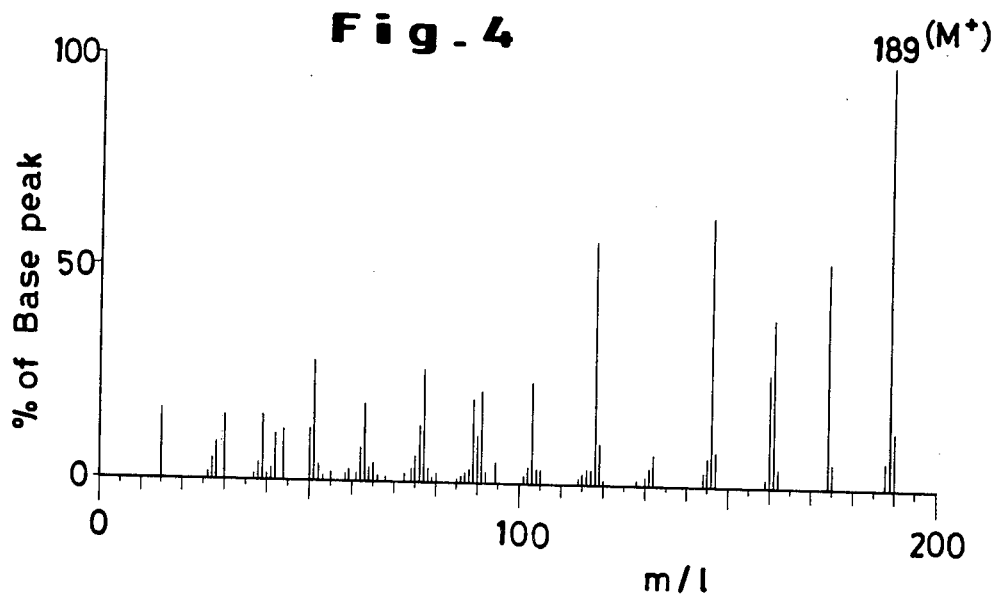
Fig_4

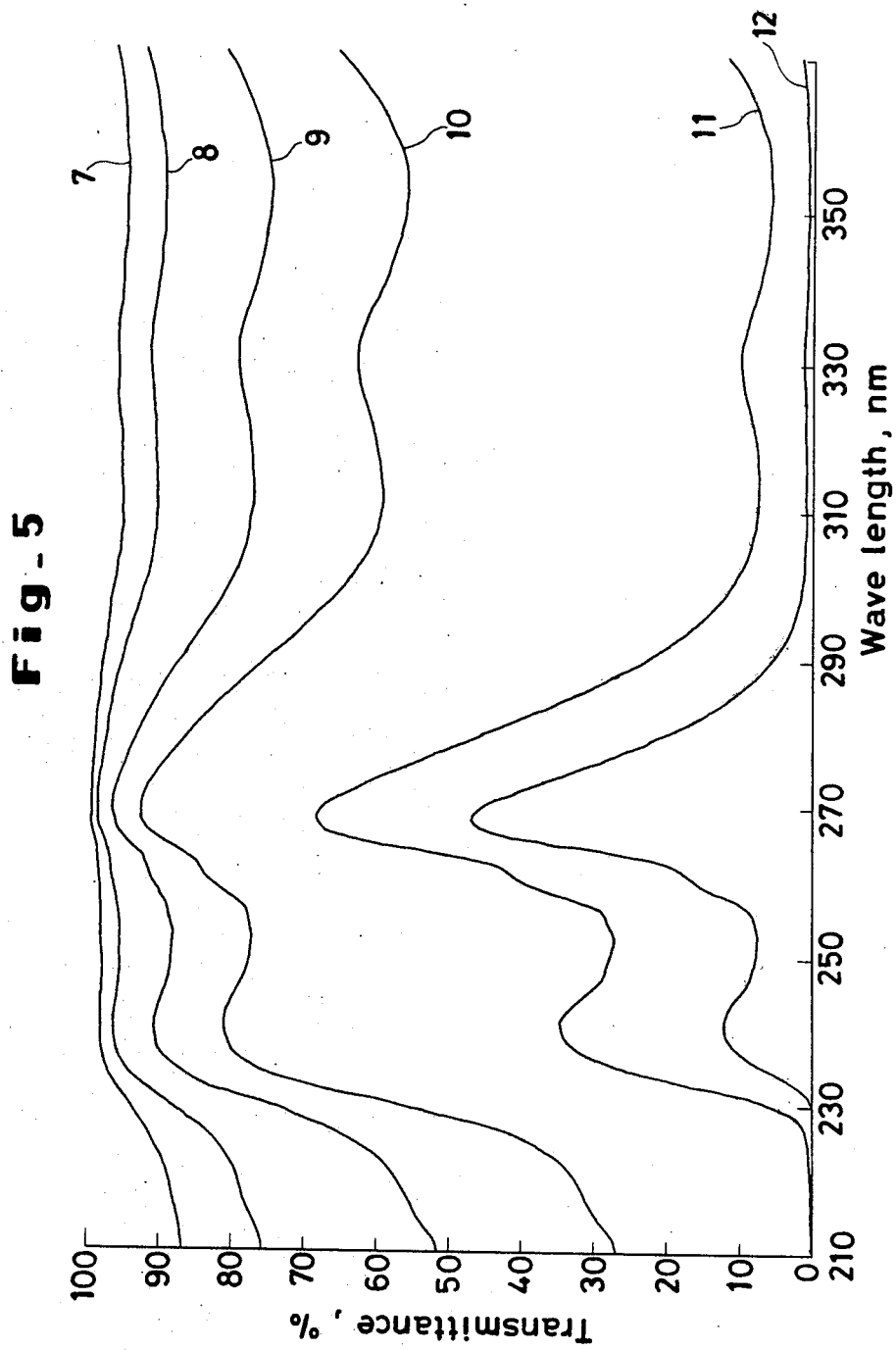

2-(N,N-DIMETHYLAMINO) INDAN-1,3-DIONE AND METHOD FOR MANUFACTURE THEREOF

BACKGROUND OF THE INVENTION

This invention relates to a novel compound having an ability to absorb ultraviolet rays and to a method for the manufacture of the compound.

There are various kinds of ultraviolet absorbents. Roughly they are grouped into benzo-phenone types, benzotriazole types and salicinic acid types. The inventor devoted a study to the development of an ultraviolet absorbent excelling the conventional ultraviolet absorbents in quality. This invention has issued from this study.

SUMMARY OF THE INVENTION 2-(N,N-dimethylamino) indan-1,3-dione represented by the structural formula:

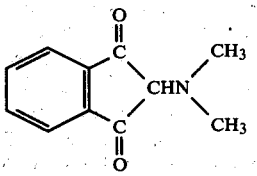

is a novel compound possessing a peculiar ultraviolet-absorbing behavior different from that of the conventional ultraviolet absorbents. It is produced by mixing 1 to 3 mols of betaine and 1 to 20 mols of acetic anhydride with 1 mol of salicylaldehyde and heating the resultant mixture.

An object of this invention is to provide a novel substance, 2-(N,N-dimethylamino) indan-1,3-dione possessing an ability to absorb ultraviolet rays.

Another object of this invention is to provide a method for the manufacture of a novel substance, 2-(N,N-dimethylamino) indan-1,3-dione possessing an ability to absorb ultraviolet rays by a very simple procedure in high yields.

BRIEF DESCRIPTION OF THE DRAWING

FIG. 3 is a nuclear magnetic resonance spectrum diagram obtained of the novel substance of the present invention.

FIG. 4 is a mass spectrum diagram obtained of the novel substance of the present invention.

FIG. 5 is an ultraviolet absorption spectrum diagram obtained of Tinuvin 326, a known ultraviolet absorbent.

DETAILED DESCRIPTION OF THE PREFERRED EMBODIMENT 2-(N,N-dimethylamino) indan-1,3-dione (hereinafter referred to briefly as DMA-indan-dione) is represented by the following structural formula.

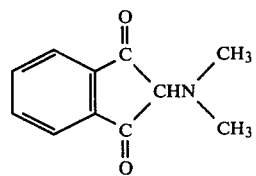

This is a novel compound which has never been reported in literature. It has been identified by various chemical constants and spectra indicated hereinbelow.

(1) Melting point—83° to 84.5° C.

(2) Solubility—Sparingly soluble in water and readily soluble in ethanol and benzene.

Figure 1:
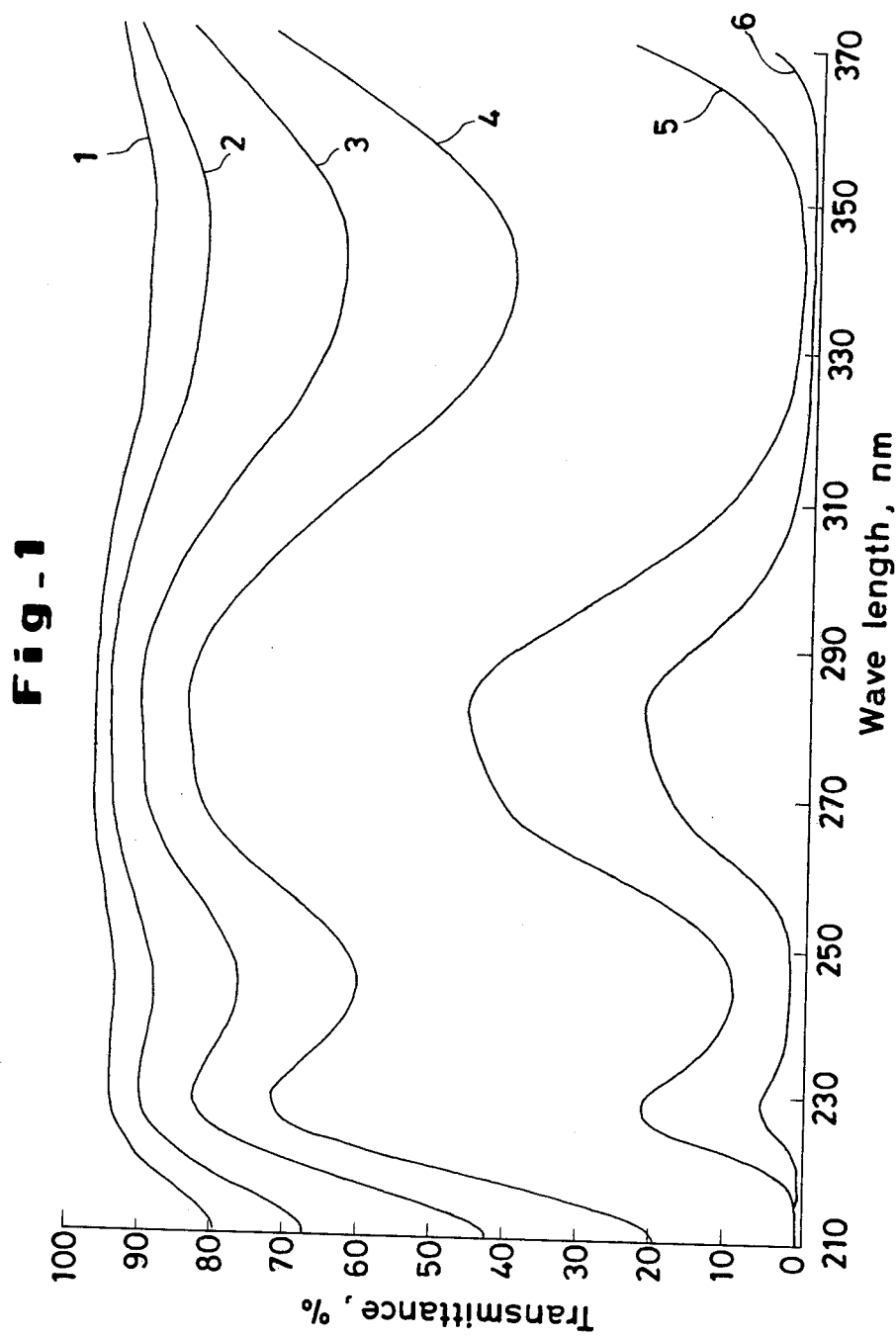
FIG. 1 is an ultraviolet absorption spectrum diagram obtained of the novel substance of the present invention.

(3) Ultraviolet absorption spectrum—The spectrum obtained by using ethanol as the solvent and a cell 10 mm in size is shown in FIG. 1, wherein the horizontal axis is graduated in terms of wave length and the vertical axis in terms of transmittance. In the diagram, the curves 1, 2, 3, 4, 5 and 6 represent the plots of absorption for the varying DMA-indan-dione concentrations 0.0005 mg/ml, 0.001 mg/ml, 0.0025 mg/ml, 0.005 mg/ml, 0.025 mg/ml and 0.05 mg/ml, respectively. It is seen from the diagram that the maximum absorptions $\lambda_{max}$ occur at 208 nm ($\epsilon$ 27,400), 246 nm ($\epsilon$ 8,100) and 340 nm ($\epsilon$ 14,400).

Figure 2:
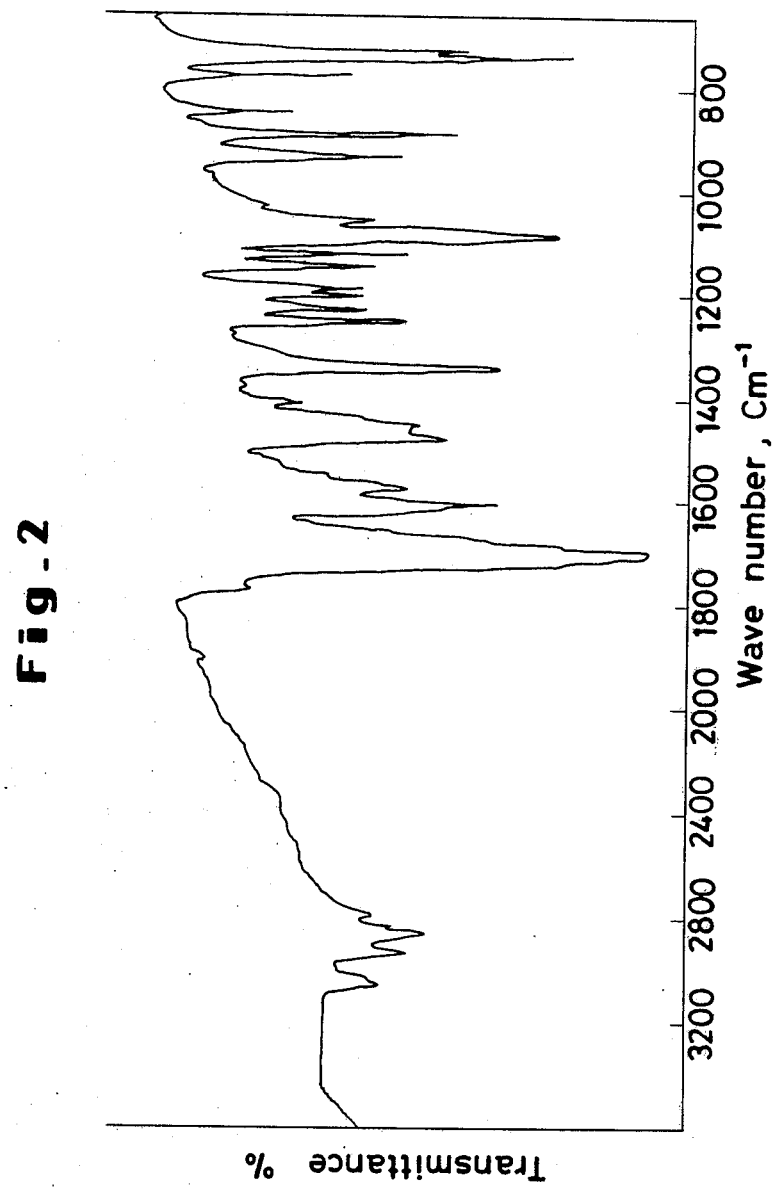
FIG. 2 is an infrared absorption spectrum diagram obtained of the novel substance of the present invention.

(4) Infrared absorption spectrum (KBR)—The spectrum obtained is shown in FIG. 2, wherein the horizontal axis is graduated in terms of wave number and the vertical axis in terms of transmittance. In the diagram the maximum absorption is found at 1705 cm$^{-1}$.

(5) Nuclear-magnetic resonance spectrum (CDCl$_3$)—The spectrum obtained is shown in FIG. 3, wherein $\epsilon$ 2.98 (6H,S), 6.69 (1H, S) and 7.27 (4H, S) are noted.

(6) Mass spectrum—The spectrum obtained is shown in FIG. 4, wherein the vertical axes are graduated in terms of % of base peak. The elementary for C$_{11}$H$_{11}$NO$_2$ at 189 (M$^t$) are as follows:
C—69.56, H—5.77, N—740 (cf. Theoretical: C—69.82, H—5.86, N—7.40).

A review of the foregoing data reveals that the presence of a diketone is confirmed by (3) and (4), the gem-CH$_3$ group, the 4H of benzene ring and the 1H on N are evident from (5), the molecular weight is indicated by the molecular ion peaks of (6) and the chemical structure is clear from the ion peaks. Thus, the chemical structure of the novel compound of this invention has been ascertained.

Now, the method for the manufacture of the novel compound, DMA-indan-dione, of the present invention will be described.

By this invention, DMA-indan-dione is produced by a one-step reaction from salicylaldehyde, betaine and acetic anhydride. To be specific, it is obtained by mixing salicylaldehyde, betaine and acetic anhydride in a molar ratio of 1:1~3:1~20, and heating the resultant mixture to induce a reaction.

The reaction is believed to proceed as shown below.

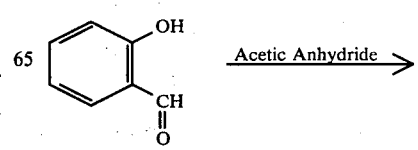

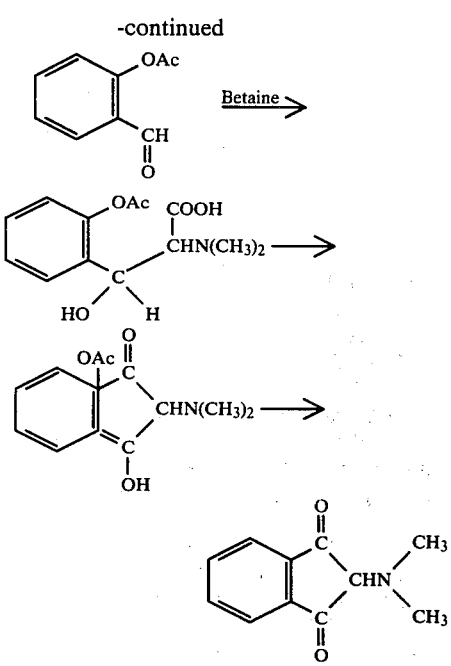

This is quite an interesting and novel reaction in that a bicyclic diketone possessing a dimethyl-amino group is derived directly from a benzene derivative.

The reason for the specific range of the molar ratio fixed as described above on the reactants, salicylaldehyde, betaine and acetic anhydride, will be described below.

The reaction proceeds very slowly and product yield is poor when the molar ratios of betaine and acetic anhydride are remarkably low. When these molar ratios exceed the respective upper limits, the product yield is poor and the crystals of DMA-indan-dione are not easily separated from the reaction mixture, making application of the reaction impractical.

Normally, the reaction does not require any solvent. The reaction proceeds advantageously to give good results when the mixture of reactants is refluxed at temperatures within the range of 100° to 200° C., preferably 150° to 170° C. The reaction proceeds slowly when the temperature of heating is low. When this temperature is too high, however, the reactants undergo decomposition and the reaction entails a secondary reaction, with the result that product yield is lowered. Practically, the reaction time is sufficient within the range of 6 to 8 hours, although it is variable with the reaction temperature involved.

When the reaction is terminated, the DMA-indan-dione is obtained in the form of light yellow prismatic crystals by expelling the volatile substance through distillation and recrystallizing the residue of distillation from benzene, ethanol, etc. In the work-up stage of the reaction, removal of acetic anhydride is achieved by treating the reactants with water.

The DMA-indan-dione is an unusually stable compound and shows strong absorption in the ultraviolet zone. This absorption, in fact, is so extensive as to cover part of the near ultraviolet zone. Thus, this compound is highly suitable as an ultraviolet absorbent.

In Table 1, the Sun Screen Indexes obtained of the DMA-indan-dione of the present invention and the known ultraviolet absorbents are compared. The Sun Screen Index indicates the absorbance obtained of an aqueous 0.1% solution of a given absorbent at 308 nm. The value of this index increases in proportion to the ultraviolet absorbing capacity of the absorvent.

TABLE 1

| Absorbent | Sun Screen Index |
|---|---|
| DMA-indan-dione | 44.0 |
| Ethyl para-dimethylamino-benzoate | 14.80 |
| Ethyl para-amino-benzoate | 9.60 |
| Isobutyl para-amino-benzoate | 9.20 |
| Para-amino benzoic acid | 7.40 |
| Salicylic acid | 4.30 |
| Menthyl salicylate | 4.00 |
| Para-amino salicyclic acid | 1.90 |
| Lauryl gallate | 0.85 |

Tinuvin 326, a benzo-triazole type compound produced by Geigy Industrial Chemical, is one of the most powerful known ultraviolet absorbents. The ultraviolet absorption spectrum obtained of Tinuvin 326 and that obtained of the DMA-indan-dione of the present invention are compared below to show the superiority of the absorbent of this invention over Tinuvin 326. The ultraviolet absorption spectrum of the DMA-indan-dione is shown in FIG. 1, while that of Tinuvin 326 is shown in FIG. 5. In the spectrometry, ethanol was used as the solvent and a cell 10 mm in size was used. In the diagram of FIG. 5, the curves 7, 8, 9, 10, 11 and 12 respectively represent the plots of absorption for the varying Tinuvin 326 concentrations of 0.0005 mg/ml, 0.001 mg/ml, 0.0025 mg/ml, 0.005 mg/ml, 0.025 mg/ml and 0.05 mg/ml.

The ultraviolet absorbing capacities of the two absorbents at 340 nm as found from FIG. 1 (DMA-indan-dione of this invention) and FIG. 5 (Tinuvin 326) are compared in Table 2 below.

TABLE 2

| Con-centration in solution | Tinuvin 326 | | DMA-indan-dione | |
|---|---|---|---|---|
| | Transmittance | Optical density | Transmittance | Optical density |
| 0.001 mg/ml | 90.2% | 0.045 | 83.0 | 0.081 |
| 0.0025 | 76.8 | 0.115 | 64.0 | 0.194 |
| 0.005 | 59.1 | 0.228 | 40.7 | 0.390 |
| 0.025 | 24 | 1.131 | 1.3 | 1.886 |

Comparison of the data of Table 2 clearly shows that the DMA-indan-dione excels Tinuvin 326 in terms of ultraviolet absorption capacity. By virtue of the characteristic property indicated above, the DMA-indan-dione produced by the present invention can be utilized as the ultraviolet absorbent in cosmetics for prevention of sunburn, paints, plastics and synthetic fibers or as the intermediate for the synthesis of dyestuffs.

Now, the present invention will be described more specifically below with reference to working examples.

EXAMPLE 1

A mixture of 1 mol of salicylaldehyde and 1 mol of betaine with a varying amount (1 mol, 2 mols, 5 mols, 10 mols or 15 mols) of acetic anhydride was placed in a reactor, there to be refluxed at 150° C. for seven hours. From the reaction mixture, light yellow crystals were obtained by expelling volatile substances from the reaction mixture through distillation and subsequently recrystallizing the residue of distillation from benzene. The crystalline product of the reaction was identified to be DMA-indan-dione, as described above, from the diagrams of infrared absorption spectrum, ultraviolet absorption spectrum, nuclear-magnetic resonance spectrum and mass spectrum. The test results of the various runs are shown in Table 3 below.

TABLE 3

| Number of mols of acetic anhydride | Yield | By-product |
|---|---|---|
| 0.2 | 3.8% | 0% |
| 1 | 23.1 | 0 |
| 2 | 44.7 | 7.3 |
| 5 | 50.9 | 27.5 |
| 10 | 48.1 | 27.1 |
| 15 | 46.0 | 24.6 |

The yields have been calculated on the basis of salicylaldehyde.

EXAMPLE 2

The procedure of Example 1 was repeated, except the amount of betaine was fixed at 2 mols and that of acetic anhydride was varied as indicated below. The crystals obtained in the test runs were identified to be those of DMA-indan-dione. The yields obtained in the various test runs are shown in Table 4 below.

TABLE 4

| Number of mols of acetic anhydride | Yield |
|---|---|
| 1 | 52.5% |
| 2 | 90.0 |
| 3 | 93.0 |

What is claimed is:
1. 2-(N,N-dimethylamino) indan-1,3-dione.
2. A method for the manufacture of 2-(N,N-dimethylamino) indan-1,3-dione, comprising the steps of mixing salicylaldehyde, betaine and acetic anhydride at a molar ratio of 1:1~3:1~20, and subsequently heating the resultant mixture.
3. The method according to claim 2, wherein the heating of the mixture is carried out at temperatures within the range of 100° to 200° C.

* * * * *